United States Patent [19]

Onore et al.

[11] 4,205,009

[45] May 27, 1980

[54] PROCESS FOR THE PREPARATION OF CYCLOPROPYLCYANIDE

[75] Inventors: Michael J. Onore; Francis J. Mettille, both of Ypsilanti, Mich.

[73] Assignee: Velsicol Chemical Corporation, Chicago, Ill.

[21] Appl. No.: 9,996

[22] Filed: Feb. 7, 1979

[51] Int. Cl.$^2$ .......................................... C07C 121/46
[52] U.S. Cl. .................................................. 260/464
[58] Field of Search ........................................ 260/464

[56] References Cited

U.S. PATENT DOCUMENTS

| 3,843,709 | 10/1974 | Bacha et al. | 260/464 |
| 3,847,985 | 11/1974 | Linder et al. | 260/464 X |
| 3,853,942 | 12/1974 | Sury et al. | 260/464 |
| 3,974,199 | 8/1976 | Plonka et al. | 260/464 |

OTHER PUBLICATIONS

Nicolet, et al., J.A.C.S., 49 (1927), pp. 2066–2071.
Cloke, J.A.C.S., 51 (1929), pp. 1174–1187.
Schlatter, J.A.C.S., 63 (1941), pp. 1733–1737.

*Primary Examiner*—Joseph Paul Brust
*Attorney, Agent, or Firm*—Dietmar Olesch; Robert J. Schwarz

[57] ABSTRACT

An improved process for the preparation of cyclopropylcyanide is disclosed. In this process, a halobutyronitrile is reacted with alkali metal hydroxide in the presence of an inert organic solvent and a catalytic amount of an anionic surfactant.

10 Claims, No Drawings

PROCESS FOR THE PREPARATION OF CYCLOPROPYLCYANIDE

BRIEF DESCRIPTION OF THE INVENTION

This invention relates to a new process for the manufacture of cyclopropylcyanide wherein halobutyronitrile is reacted with solid alkali metal hydroxide in the presence of an inert organic solvent and a catalytic amount of an anionic surfactant.

DETAILED DESCRIPTION OF THE INVENTION

Cyclopropylcyanide has proven to be a valuable as well as a versatile compound. It is a source of the cyclopropyl group and, thus, is useful in the preparation of agricultural chemicals whose performance characteristics are improved by the presence of the cyclopropyl group; one such class of chemicals is, e.g., the N-cycloalkyl anilines.

Prior art methods for preparing cyclopropylcyanide have involved reacting a halobutyronitrile with an alkali metal hydroxide or sodium amide; these reactions generally are conducted at high temperatures. The use of potassium and sodium hydroxides is disclosed in Nicolet et al., Journal of the American Chemical Society, 49, 2068 (1927) and Cloke, Journal of the American Chemical Society, 51, 1180 (1929). The use of sodium amide is disclosed in Schlatter, Journal of the American Chemical Society, 63, 1734 (1941).

Certain problems have been encountered with these prior art procedures. Substandard yields of product have generally been obtained with them; the reaction with the hydroxide generally gives yields of from 40–50%, while the reaction with the amide gives yields of about 60%. These low yields have generally resulted from troublesome side reactions as well as difficult and prolonged distillation procedures.

Furthermore, the prior art procedures have not been readily adaptable to commercial scale up; this is due, in part, to the potentially violent reaction with sodium amide and to the aforementioned prolonged distillation procedures.

U.S. Pat. No. 3,853,942 discloses a process for the preparation of cyclopropylcyanide by reacting halobutyronitrile with an alkali metal alkoxide in an inert solvent at elevated temperatures and removing the alcohol formed. However, the alkali metal alkoxide is a reactant which is relatively expensive and is difficult to handle; thus, when possible, it is desirable to avoid the use of this materials.

SUMMARY OF THE INVENTION

In accordance with this invention, there is provided a process for the preparation of cyclopropylcyanide comprising reacting a 4-halobutyronitrile selected from the group consisting of 4-chlorobutyronitrile, 4-bromobutyronitrile, 4-iodobutyronitrile, and mixtures thereof with from about 1.0 to about 3.5 moles of a solid alkali metal hydroxide per mole of said 4-halobutyronitrile in the presence of an inert organic solvent and a catalytic amount of an anionic surfactant.

DESCRIPTION OF THE PREFERRED EMBODIMENTS

The novel process of this invention is seen to proceed according to the following equation:

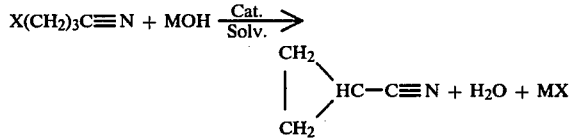

wherein X is selected from chlorine, iodine, or bromine; and M is an alkali metal or alkaline earth metal.

Thus, 4-chlorobutyronitrile, 4-bromobutyronitrile, 4-iodobutyronitrile, and mixtures thereof are applicable for use in the process of this invention. The 4-chlorobutyronitrile is the preferred halobutyronitrile. Methods for preparing such nitriles are known; reference in this regard may be made to the JACS articles and U.S. Pat. No. 3,853,942 noted hereinabove. These nitriles are typically prepared by the anhydrous free radical reaction of allyl chloride and hydrogen halide in the presence of benzoyl peroxide followed by the reaction of the resulting trimethylenechlorohalide, in 50% excess, with sodium cyanide in ethanol-water medium.

The second reactant utilized in the process of this invention is a solid alkali metal hydroxide. The useful alkali metals of the first column of the periodic table are lithium, sodium, potassium and rubidium, with sodium and potassium being particularly preferred.

In the process of this invention, the alkali metal hydroxide is in a solid phase and is reacted with the 4-halobutyronitrile; the latter reactant is in the liquid phase. Preferred as second reactants are potassium hydroxide and sodium hydroxide. In carrying out this process, useful results are obtained when the ratio of nitrile reactant to hydroxide reactant is in the range of from about 1:1 to about 1:3.5 and more preferably from about 1:1.2 to about 1:2.5 moles. A very useful molar ratio of nitrile to hydroxide is about 1:1.5 to about 1:2. Since there is a need to avoid hydrolysis of the cyclopropanecarbonitrile final product (which is often called "cyclopropylnitrile" for convenience), it is beneficial to employ larger than stoichiometric amounts of the hydroxide in order to increase the reaction rate. In carrying out the process of this invention, the hydroxide can be in any of the ususal solid forms commercially available, such as, e.g., flake, pellet, powder, beads or pells.

The reaction is conducted in an inert organic solvent, the choice of solvent being dependent upon the temperature at which it is desired to conduct the reaction. Suitable solvents for use in the process of this invention include non-fused ring aromatics such as benzene, toluene, and xylene; lower haloalkanes and lower haloalkylenes having 1 to 6 carbon atoms such as methylene chloride, trichlorotrifluoroethane, 1,2-dichloroethylene, carbontetrachloride, trichloroethylene, and tetrachlorodifluoroethane alkanes of 5 to 8 carbon atoms such as pentane, hexane, heptane, and octane; and petroleum ethers which are various hydrocarbon mixtures of the foregoing alkanes, as well as cycloalkanes and cycloalkylenes such as cyclohexane, cyclohexene, and cyclopentane. Combinations of these solvents may be employed to achieve a particular combination of reaction temperatures; thus, e.g., a mixture of toluene and methylene chloride may be used. Particulary preferred inert organic solvents are benzene, toluene and methylene chloride, with methylene chloride being the solvent of choice.

The amount of solvent can vary over a large range with the least amount of solvent being that sufficient to have a workable reaction slurry with sufficient volume to dissipate the heat generated by the reaction. For instance, when benzene, toluene or methylene chloride is the solvent, as little as one volume of solvent can be successfully employed to three volumes of the nitrile reactant; and a volume ratio of one to one is quite suitable. Larger amounts, such as three to one hundred volumes of solvent per volume of nitrile reactant, are also usable, although the volumes of solvent are less convenient to handle.

The anionic surfactant is an essential component required in the practice of the present invention. The amount of anionic surfactant which can be used can vary from a small amount, such as 0.0002 moles or less per mole of the nitrile reactant, up to an amount exceeding the stoichiometric amount required to displace the halogen component of the nitrile reactant. The amount of catalyst preferably used is from about 0.002 to about 0.10 moles per mole of nitrile reactant; it is more preferred to use from about 0.002 to about 0.02 moles of surfactant per mole of nitrile reactant. On a weight by weight basis, one should use at least about 0.1 percent of surfactant by weight of halobutyronitrile reactant. It is preferred to use at least 0.5 percent (by weight) of said surfactant; and it is more preferred to use at least 1.0 percent (by weight) of said surfactant. In the most preferred embodiment, one should use at least about 2.0 percent (by weight of halobutyronitrile reactant) of said surfactant. A detailed discussion of the chemistry, properties, and uses of anionic surfactants useful in applicant's process is presented in Kirk-Othmer's "Encyclopedia of Chemical Technology", Second Edition, Volume 19, pp. 507–591, John Wiley & Sons, Inc., New York, 1969; this article is hereby incorporated by reference in toto into this application.

The preferred anionic surfactants which may be used in the process of this invention are characterized by being soluble in at least one phase of a liquid system; by having amphipathic structure (the surfactant molecules are composed of groups with opposing solubility tendencies); by having their molecules or ions form oriented monolayers at phase interfaces; by having the equilibrium concentrations of their solutes at phase interfaces be greater than their concentrations in the bulk of the solutions; by forming aggregates of molecules or ions called micelles when the concentrations of the solutes in the bulk of the solutions exceed a limiting value; and by having their solutions exhibit at least one of the properties of detergency, foaming, wetting, emulsifying, solubilizing, and dispersing.

The surfactants used in the process of this invention contain both water-soluble and water-insoluble moieties in their molecules. The preferred anionic surfactants which may be used in the process of this invention contain a hydrophilic, solubilizing moiety which is a polar group that is negatively charged in aqueous solutions or dispersions. It is preferred that said anionic solubilizing group be selected from the group consisting of carboxylates, sulfonates, sulfates, and phosphates.

When the anionic surfactant contains a carboxylate solubilizing group, it is preferred that said surfactant be selected from the group consisting of soaps and aminocarboxylates. The preferred soaps which may be used in the process of this invention are described by the formula $(RCOO)^-(M)^+$ wherein R is an alkyl group containing from about 9 to about 21 carbon atoms and M is a metallic or amine ion. The preferred aminocarboxylate surfactants which may be used in the process of this invention are selected from the group consisting of N-acylsarcosinates and acylated protein hydrolysates. The N-acylsarcosinates are preferably described by the formula $(R^1COO)^-(M^1)^+$ wherein said $(R^1COO)^-$ group is selected from the group consisting of cocoyl, lauroyl, oleoyl, stearoyl, and tall oil acyl and said $(M^1)^+$ cation is selected from the group consisting of hydrogen and sodium. The preferred acylated protein hydrolysates are prepared from protein hydrolysates by acylation with fatty acid chlorides or by direct condensation with fatty acids; they may be described by the formula (Fatty acid/Peptide Condensate)$^-(M^2)^+$ wherein said $M^2$ is preferably selected from the group consisting of sodium and potassium.

When the anionic surfactant contains a sulfonate solubilizing group, it is preferred that said sulfonate be of the formula $R^2SO_3Na$ wherein $R^2$ is a biodegradable hydrocarbon group in the surfactant molecular weight range; thus, e.g., alkylbenzenesulfonates petroleum sulfonates, sulfosuccinates, naphthalenesulfonates, N-acyl-N-alkyltaurates, $\beta$-sulfoesters of fatty acids, and $\alpha$-olefin sulfonates may be used in the process of this invention. Other anionic sulfonate surfactants known to those skilled in the art also may be used in the process of this invention.

One of the surfactants which may be used in the process of this invention is selected from the group consisting of (1) a nonionic/anionic blend of an isopropyl amine salt of dodecylbenzene sulfonic acid and an ethoxylated alcohol containing from 10 to 18 carbon atoms and (2) an oil soluble metal sulfonate and a polyoxyethylene ether blended in proportions such that the surfactant possesses a hydrophile liphophile balance of from about 10 to about 14. The latter emulsifying agent is preferred; an additional description of it appears in U.S. Pat. No. 3,729,434, which patent is hereby incorporated herein by reference. It should be noted that one can also use "matched pairs"—a surfactant with a hydrophile liphophile balance of from about 10 to about 14 prepared by blending a surfactant with a hydrophile liphophile value of less than 10 with a surfactant having a hydrophile liphophile value of greater than 14.

Alkylbenzenesulfonate surfactants also may be used in the process of this invention. Some of the preferred alkylbenzene sulfonate surfactants which may be used in the process of this invention are described by the formula $R^3C_6H_4SO_3M^3$ wherein $R^3$ is selected from the group consisting of dodecyl, tridecyl, linear dodecyl, linear tridecyl, and nonyl and $M^3$ is selected from the group consisting of hydrogen, sodium, ammonium, calcium, triethanolamine, and amine.

The preferred petroleum sulfonate surfactants contain alkylaromatic hydrocarbon sulfonates.

Dialkyl sulfosuccinates are also useful in the process of this invention. It is preferred to use the sodium salt of these sulfosuccinate esters. In the most preferred class of sodium dialkyl sulfosuccinates, the alkyl group is selected from the group consisting of amyl, hexyl, 2-ethylhexyl, tridecyl, octyl, and isobutyl.

Naphthalenesulfonates are another class of sulfonate surfactants which may be used in the process of this invention. Some of the more preferred naphthalenesulfonates are described by the formula $(R^4C_{10}H_6SO_3^-)(M^{4+})$ wherein $R^4$ is selected from the group consisting of isopropyl, tetrahydro, butyl, nonyl, condensed formaldehyde, and complex dimethyl and $M^4$ is selected from the group consisting of hydrogen and sodium.

The N-acyl-N-alkyltaurates are another class of sulfonate surfactants which may be used in the process of this invention. A preferred class of said taurates is described by the formula $R^5R^6NCH_2CH_2SO_3Na$ wherein $R^5$ is selected from the group consisting of oleoyl, coco acyl, palmitoyl, tall oil, and tallow and $R^6$ is selected from the group consisting of cyclohexyl and methyl.

Another class of sulfonate surfactants which are useful are the 2-sulfoethyl esters of fatty acids.

The anionic surfactant may contain a sulfate solubilizing group. One preferred class of sulfate surfactants is described by the formula $R^7OSO_3M^5$ wherein $R^7$ is selected from the group consisting of lauryl, 2-ethylhexyl, cetyl, oleyl, tallow, octyl, myristyl, tridecyl, $C_{14}H_{29}$, and $C_{17}H_{35}$ and $M^5$ is selected from the group consisting of sodium, ammoniuum, potassium, diethanolamine, triethanolamine, and magnesium. Another preferred class of sulfate surfactants is described by the formula $R^8C_6H_4(OCH_2CH_2)_nOSO_3M^6$. In these sulfated and ethoxylated alkylphenols, $R^8$ is selected from the group consisting of alkyl of 1 to 18 carbon atoms such as, e.g., nonyl, $M^6$ is selected from the group consisting of sodium, ammonium, and triethanolamine, and n is from about 2 to about 6.

Natural fats and oils such as castor oil and sperm oil may be used in the process of this invention. The disodium salt of sulfated oleic acid also is useful in practicing the process of this invention. Sulfated alkanolamides of the formula $R^9CONHCH_2CH_2OSO_3M^7$ where $R^9$ is alkyl containing from about 2 to about 20 carbon atoms and $M^7$ is a metal selected from the group consisting of alkali and alkaline earth metals such as, e.g., sodium and potassium, also may be used in the process of this invention.

Another class of sulfated surfactants which may be used in the process of this invention is the sulfated esters. A preferred class of these sulfated esters is described by the formula $R^9CH(OSO_3M^7)CH_2R^{10}CH_2COOR^{11}$ wherein $R^9$ and $M^7$ are as hereinbefore described, $R^{10}$ is alkylene containing from about 2 to about 20 carbon atoms, and $R^{11}$ is alkyl containing from about 1 to about 10 carbon atoms such as, e.g., propyl, butyl, and amyl.

Ethoxylated and sulfated alcohols of the formula $R^9(OCH_2CH_2)_nOSO_3M^7$ wherein n is from about 1 to about 8 also may be used in the process of this invention. The anionic surfactant may contain a phosphate solubilizing group. Some of the components of the preferred phosphate ester surfactants which may be used in the process of this invention include, e.g., 2-ethylhexyl phosphate, octyl phosphate, decyl phosphate, dodecylphosphate, octadecyl phosphate, 9-octadecenyl phosphate, hexyl polyphosphate, 2-ethylhexyl polyphosphate, octyl polyphosphate, decyl polyphosphate, 2-ethylhexanol (both ethoxylated and phosphated), phosphated isoctyl alcohol, phosphated dodecyl alcohol, phosphated tridecyl alcohol, phosphated 9-octadecen-1-ol, phosphated phenol, phosphated octylphenol; phosphated dodecylphenol; phosphated dinonylphenol; phosphated nonylphenol, and the like; the cations of these preferred phosphate ester surfactants are selected from the group consisting of hydrogen, sodium, potassium, morpholine, triethanolamine, and barium.

At least one anionic surfactant is used in the process of this invention. However, one may blend other surfactants (such as, e.g., another anionic surfactant, a nonionic surfactant, a cationic surfactant, an amphoteric surfactant, or any combination of one or more of these with the others) with the anionic surfactant and use the blend containing the anionic surfactant in the process of this invention. In one preferred embodiment, a blend of a nonionic surfactant with an anionic surfactant is used in the process of this invention.

The anionic surfactants which may be used in the process of this invention and the blends of surfactants containing anionic surfactants which may be used in said process are described in detail in Kirk-Othmer's "Encyclopedia of Chemical Technology", Second Edition, Vol. 19, pp. 517–591, op. cit.

By way of illustration and not limitation, some of the surfactants which may be used in the process of this invention include, e.g., Abex ® 18S, 22S, 26S, VA-40, and VA-50 surfactants sold by Alcolac, Inc.; Acto ® 450, 500, 630, 632 and 639 alkaryl sodium sulfonates sold by the Exxon Company; Acylglutamate LS-11 monosodium N-lauroyl-L-glutamate surfactant sold by Ajinomoto; Aerosol 19 disodium N-octadecylsulfosuccinamate emulsifier sold by the American Cyanamide company; Agrimul ® A-300 aromatic sulfonate-oxide condensate blend emulsifier sold by the Diamond Shamrock Company; Alcopol ® FL tetra sodium N(1-2 dicarboxy ethyl) N-octadecyl sulphosuccinamate emulsifying agent sold by Allied Colloids, Inc.; Alkanol ® S Flakes sodium tetrahydronaphthalene sulfonate dispersant sold by the DuPont Company; Atlox ® 3403 anionic/anionic formulated product emulsifier sold by ICI United States; Atlox ® 3404F nonionic/anionic formulated product emulsifier with a hydrophile liphophile balance of 10.0 which is sold by ICI United States; Atlox ® 3406 nonionic/anionic formulated product emulsifier with a hydrophile liphophile balance of 12.0 which is sold by ICI United States; Atlox ® 3408F nonionic/anionic formulated product emulsifier with a hydrophile liphophile balance of 13.0 which is sold by ICI United States; sodium laureth sulfate; sodium lauryl sulfate; sodium 2-ethylhexyl sulfate; sodium N-decyl sulfate; sodium tridecyl sulfate; sulfated castor oil; the sodium slat of a sulfonated naphthalene-formaldehyde condensate; Calsoft ® LAS 99 linear alkyl benzene sulfonic acid emulsifier sold by the Pilot Chemical Company; sodium 2-ethyl-1-hexyl sulfate; glyceryl monostearate; Carsofos ® NP-9anionic mono and dialkylarylphenoxy polyoxyethylene acid phosphates sold by the Carson Chemical Company; magnesium lauryl sulfate; Cepedon ® AM amine salt of linear dodecyl benzene sulfonic acid sold by the Chemical Developments of Canada Ltd.; triethanolamine dodecyl benzene sulfonate; sodium cetyl sulfate; sodium oleyl sulfate; sodium myristal sulfate; Decersol ® Surfactant P Special anionic/nonionic modified alkylarylsulfonate detergent sold by the American Cyanamid Company; sodium dodecyl diphenyloxide disulfonate; butyl naphthalene sodium sulfonate. Other anionic surfactants well known to those skilled in the art also may be used in the process of this invention. Thus, e.g., the anionic surfactants described in McCutcheon's "Detergents and Emulsifiers", North American Edition, 1977 Annual (McCutcheon Division, MC Publishing Company, Glen Rock, New Jersey) may be used in the process of this invention; said McCutcheon's publication is hereby incorporated by reference into this application.

In a preferred embodiment, the anionic surfactant used in the process of this invention contains at least one sulfonate solubilizing group. In a more preferred embodiment, said surfactant is a blend of a nonionic surfactant with an anionic surfactant containing at least one sulfonate solubilizing group, and said blended surfactant has a hydrophile liphophile balance of from about 10 to about 14.

The conditions under which the process of this invention may be conducted can vary depending upon the reactants employed. Since reaction pressures can vary from superatmospheric to subatmospheric, the reaction temperatures can be substantially higher than 100 degrees centigrade or even lower than 40 degrees centigrade. Careful selection of reaction temperatures and pressures can minimize the formation of undesirable byproducts, and such selection of optimum reaction temperatures, pressures and other operating conditions therefore constitutes a preferred embodiment of this invention. Preferred reaction temperatures for halobutyronitrile and alkali metal hydroxides range from about 40 degrees to about 150 degrees centigrade, and more preferably from about 50 degrees to about 120 degrees centigrade. A reaction temperature of from about 60 degrees to about 110 degrees centigrade is particularly preferred. Reaction pressure are most conveniently maintained at atmospheric pressure, but pressures from 0.1 or less up to 10 or more atmospheres are included with the scope of this invention.

From the foregoing discussion it will be seen that the time of conducting the reaction will vary over a considerable time span depending upon the temperature employed (which will generally be from a few minutes to up to about 10 hours). It is an advantage of the process of this invention that as soon as all of the nitrile reactant has been consumed in the reaction, the reaction can be terminated without the post-holding or treating period typical of many other reactions. The elimination of this post-holding period reduces the possibility of hydrolysis of the cyclopropanecarbonitrile final product obtained. In general, the formation of a high proportion of cyclopropanecarbonitrile can be obtained by conducting the reaction at a temperature below 110 degrees centigrade.

As previously indicated, this process ensures the formation of pure cyclopropanecarbonitrile in high yields. The resulting compound may then be further synthesized into biologically active materials for agricultural and pharmaceutical application. For example, the cyclopropanecarbonitrile may be reacted with n-propylamine in the presence of a platinum metal catalyst to form cyclopropylmethylpropylamine which can then be reacted according to the disclosures of U.S. Pat. No. 3,546,295 to prepare N-cycloalkylaniline herbicidal compounds. Alternately, the cyclopropanecarbonitrile may be converted to cyclopropylamine which may, in turn, be reacted with cyanuric chloride to form cyclopropylamino-substituted-s-triazine herbicides.

The following examples are included to illustrate the process of the present invention but are not to be considered limitative thereof. Unless otherwise specified, all parts are by weight, all temperatures are in degrees centigrade, and all volumes are in milliliters.

EXAMPLE 1

To a one-liter, round bottom flask fitted with a stirrer, Dean-Stark trap, thermometer, and reflux condenser were charged 250 millimeters of benzene, 115 grams (1.0 moles) of a mixture (in a 3/1 weight ratio) of 4-chlorobutyronitrile and 4-bromobutyronitrile, 60 grams (1.5 moles) of reagent sodium hydroxide pellets, and 2.3 grams of Atlox ® 3408F (a nonionic/anionic blend of surfactants with a hydrophile liphophile balance of 13.0 whose anionic component contains a sulfate solubilizing group and which is commercially available from ICI America, Inc.). The reaction mixture was heated to reflux.

During the reaction, samples were taken at regular intervals and subjected to gas chromatographic analyses to determine how far the reaction had proceeded. Gas chromatographic analyses were conducted on a Varian 1700 gas chromatograph equipped with a 10 percent Reoplex 400 on Chromasborb W column (6'×¼") at 160 degrees Centigrade; results were based on a weight standard of an authentic standard of cyclopropylcyanide. The results of these analyses are shown below.

| Time | Percent of Halobutyronitrile Which Remained Unreacted |
|---|---|
| 1 hour | 91 |
| 3 hours | 62 |
| 4 hours | 34 |
| 5 hours | 06 |

The reaction was terminated after about 5.5 hours. At this point, the mixture was cooled to ambient temperature, and 250 millimeters of water were added to dissolve all salts present. The phases were separated, and the aqueous phase was extracted with 50 millimeters of benzene to obtain additional cyclopropylcyanide dissolved in the water. The benzene layers were combined; 58.8 grams of cyclopropylcyanide were obtained in a yield (assuming a 95 percent conversion of the crude nitrile reactant) of 92.3 percent.

EXAMPLE 2

The procedure of Example 1 was repeated, and the reaction was terminated after 5.5 hours. About 60.9 grams of cyclopropylcyanide were obtained in a yield (assuming a 95 percent conversion of the crude nitrile reactant) of 93.6 percent.

EXAMPLE 3

The procedure of Example 1 was repeated with the exception that 2.3 grams of Atlox ® 3403F (a nonionic/anionic surfactant blend whose anionic component contains a sulfonate solubilizing group and which is commercially available for ICI America, Inc.) was substituted for the 2.3 grams of Atlox ® 3408F used in Example 1. During the reaction, samples were taken at regular intervals and subjected to gas chromatographic analyses to determine how far the reaction had proceeded; the results of these analyses are shown below.

| Time | Percent of Halobutyronitrile Which Remained Unreacted |
|---|---|
| 1 hour | 89 |
| 2 hours | 78 |
| 3 hours | 67 |
| 4 hours | 53 |
| 5 hours | 28 |
| 6 hours | 05 |

The reaction was terminated after 6.5 hours. Sixty-one point nine grams of cyclopropylcyanide were obtained in a yield (assuming a 95 percent conversion of the crude nitrile reactant) of 97.1 percent.

COMPARATIVE EXAMPLE 4

The procedure of Example 1 was repeated with the exception that 2.3 grams of Emulsifier 222 (a nonionic aryl polyoxy ether emulsifier commercially available from the Milliken Chemical Corporation) were substituted for the 2.3 grams of Atlox ® 3408F used in Example 1. During the reaction, samples were taken at regular intervals and subjected to gas chromatographic analyses to determine how far the reaction had proceeded; the results of these analyses are shown below.

| Time | Percent of Halobutyronitrile Which Remained Unreacted |
| --- | --- |
| 1 hour | 96 |
| 3 hours | 86 |
| 4 hours | 78 |
| 5 hours | 72 |

COMPARATIVE EXAMPLE 5

The procedure of Example 1 was repeated with the exception that no surfactant or emulsifier was present in the reaction mixture. During the reaction, samples were taken at regular intervals and subjected to gas chromatographic analyses to determine how far the reaction had proceeded; the results of these analyses are shown below.

| Time | Percent of Halobutyronitrile Which Remained Unreacted |
| --- | --- |
| 1 hour | 96 |
| 4 hours | 77 |
| 6 hours | 67 |
| 7.5 hours | 55 |

This invention provides a vastly improved process for the preparation of cyclopropylcyanide. The foregoing examples and methods have been described in this specification for the purpose of illustration and not limitation. Many other modifications and ramifications will naturally suggest themselves to those skilled in the art based upon this disclosure; they are intended to be comprehended as within the scope of this invention.

The embodiments of this invention in which an exclusive property or privilege is claimed are defined as follows:

1. A process for the preparation of cyclopropylcyanide comprising reacting a 4-halobutyronitrile selected from the group consisting of 4-chlorobutyronitrile, 4-bromobutyronitrile, 4-iodobutyronitrile, and mixtures thereof with from about 1.0 to about 3.5 moles of solid alkali metal hydroxide per mole of 4-halobutyronitrile reactant in the presence of an inert organic solvent and a catalytic amount of an anionic surfactant at a temperature of from about 40 to about 150 degrees centigrade and at a pressure of from about 0.1 to about 10 atmospheres.

2. The process of claim 1, wherein said alkali metal hydroxide is selected from the group consisting of sodium hydroxide and potassium hydroxide.

3. The process of claim 2, wherein at least about 0.1 percent of said anionic surfactant by weight of said 4-halobutyronitrile is present in the reaction mixture.

4. The process of claim 3, wherein said surfactant has a hydrophile liphophile balance of from about 10 to about 14.

5. The process of claim 4, wherein said reaction is conducted at a room temperature of from about 50 to about 120 degrees centigrade.

6. The process of claim 5, wherein there are from about 1.2 to about 2.5 moles of said alkali metal hydroxide per mole of 4-halobutyronitrile reactant.

7. The process of claim 6, wherein said reaction is conducted at a temperature of from about 60 to about 110 degrees centigrade.

8. The process of claim 7, wherein said alkali metal hydroxide is sodium hydroxide.

9. The process of claim 8, wherein said surfactant is a blend of a nonionic surfactant with an anionic surfactant containing at least one sulfonate solubilizing group.

10. The process of claim 9, wherein there are from about 1.5 to 2.0 moles of sodium hydroxide per mole of 4-halobutyronitrile reactant.

* * * * *